(12) United States Patent
Kim et al.

(10) Patent No.: US 12,340,473 B2
(45) Date of Patent: Jun. 24, 2025

(54) GUIDANCE METHOD FOR MOTOR IMAGERY AND APPARATUS THEREOF

(71) Applicant: RESEARCH & BUSINESS FOUNDATION SUNGKYUNKWAN UNIVERSITY, Suwon-si (KR)

(72) Inventors: Jonghyun Kim, Seoul (KR); Hojun Jeong, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 358 days.

(21) Appl. No.: 17/945,732

(22) Filed: Sep. 15, 2022

(65) Prior Publication Data

US 2023/0078964 A1    Mar. 16, 2023

(30) Foreign Application Priority Data

Sep. 15, 2021    (KR) .......................... 10-2021-0123105

(51) Int. Cl.
| | | |
|---|---|---|
| G06T 19/00 | (2011.01) | |
| G02B 27/01 | (2006.01) | |
| G06F 3/01 | (2006.01) | |
| G06F 3/14 | (2006.01) | |
| G06T 19/20 | (2011.01) | |
| G06V 10/25 | (2022.01) | |
| G06V 40/20 | (2022.01) | |

(52) U.S. Cl.
CPC .......... *G06T 19/006* (2013.01); *G02B 27/017* (2013.01); *G06F 3/015* (2013.01); *G06F 3/016* (2013.01); *G06F 3/14* (2013.01); *G06T 19/20* (2013.01); *G06V 10/25* (2022.01); *G06V 40/20* (2022.01)

(58) Field of Classification Search
None
See application file for complete search history.

(56) References Cited

U.S. PATENT DOCUMENTS

| | | | |
|---|---|---|---|
| 2011/0080273 A1 | 4/2011 | Kawai et al. | |
| 2013/0035612 A1* | 2/2013 | Mason ................. | A61B 5/1128 600/595 |

FOREIGN PATENT DOCUMENTS

| | | | | |
|---|---|---|---|---|
| JP | 5419100 B2 | 2/2014 | | |
| KR | 10-2016-0092836 A | 8/2016 | | |
| WO | WO-2010022882 A2 * | 3/2010 | ............... | A61F 4/00 |

(Continued)

OTHER PUBLICATIONS

Evans, Nathan, et al. "Shared electrophysiology mechanisms of body ownership and motor imagery." Neuroimage 64 (2013): 216-228.

(Continued)

*Primary Examiner* — Thomas D Lee
(74) *Attorney, Agent, or Firm* — NSIP Law

(57) ABSTRACT

Provided is a technique that trains motor imagery to reinforce brain waves, and a guidance method for motor imagery displays virtual reality including a virtual body part corresponding to a user's real body part the user, detects a movement of the real body part through a motion sensor to track a motion, and visually displays the movement of the virtual body part through the virtual reality according to the tracked motion to induce an ownership feeling that makes the user mistake the virtual body part for the real body part.

17 Claims, 9 Drawing Sheets

(56) References Cited

FOREIGN PATENT DOCUMENTS

| WO | WO-2011123059 A1 | * | 10/2011 | ......... | A61B 5/04014 |
| WO | WO-2014186739 A1 | * | 11/2014 | ......... | A63B 24/0075 |

OTHER PUBLICATIONS

Korean Office Action issued on Mar. 31, 2023, in counterpart Korean Patent Application No. 10-2021-0123105 (11 pages in Korean).

* cited by examiner

[FIG. 1]

[FIG. 2]
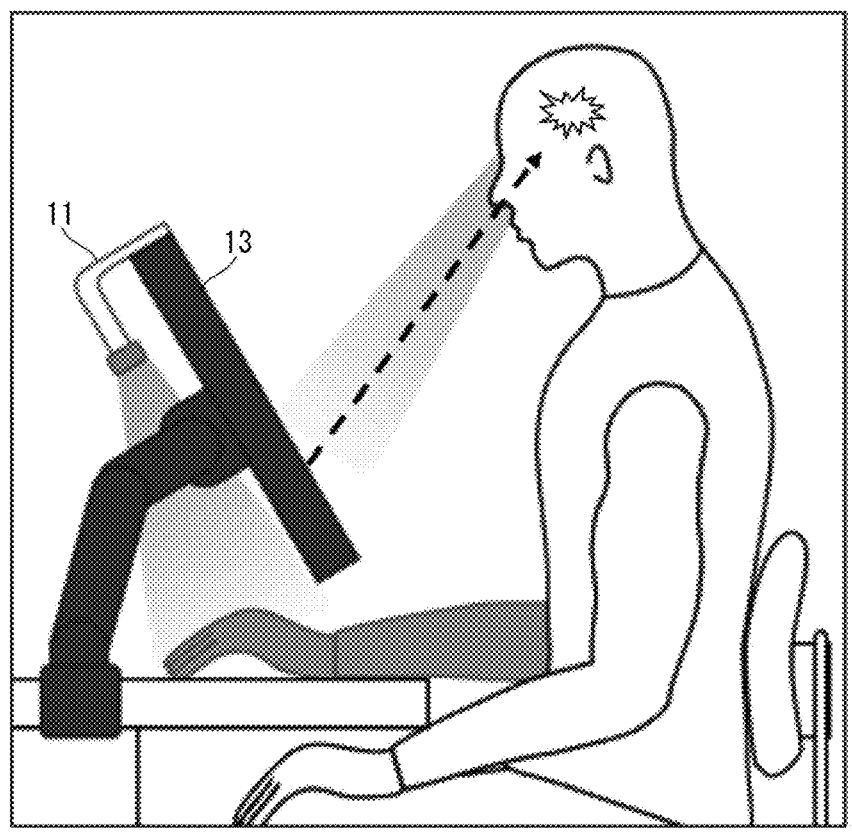
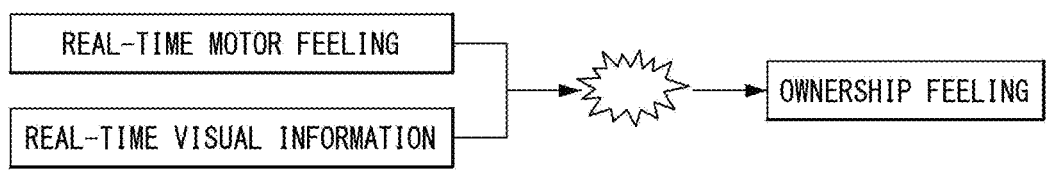

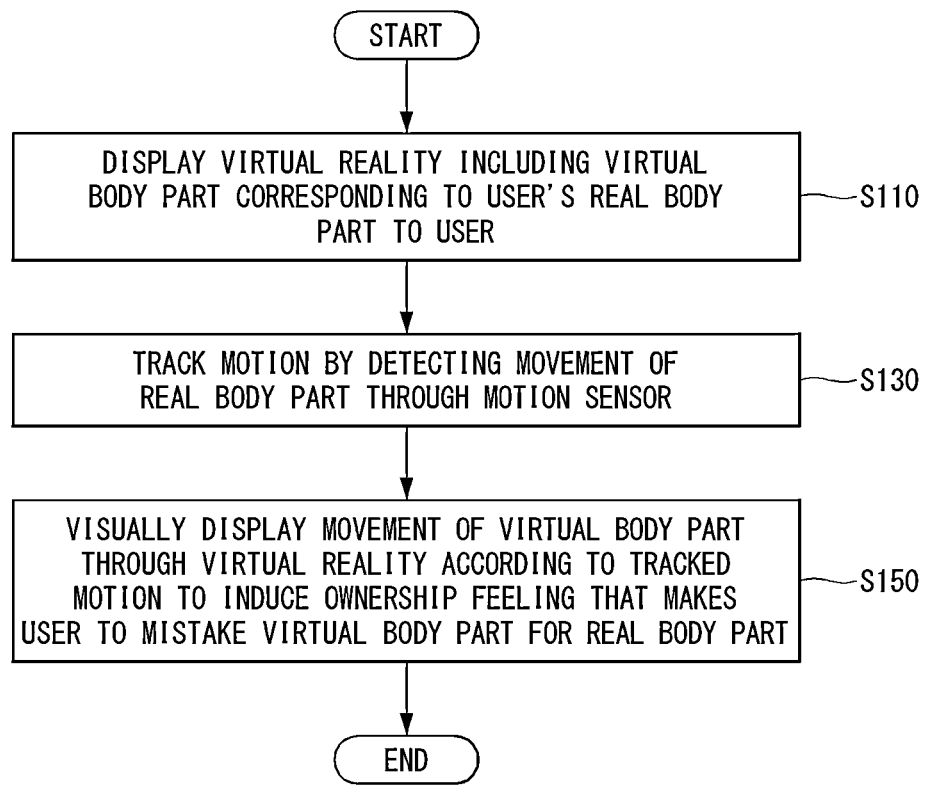

[FIG. 4]
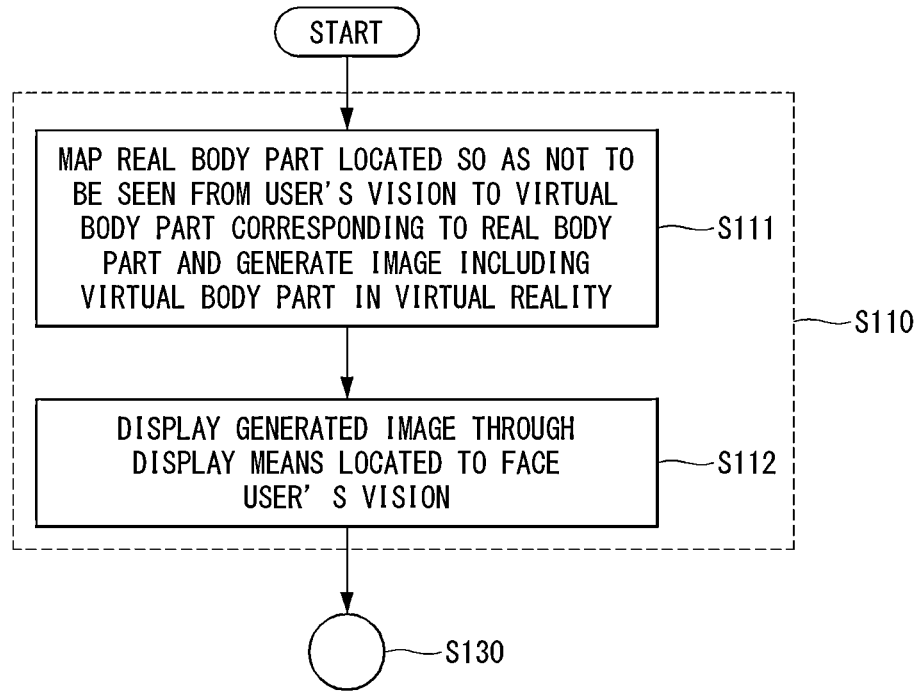
[FIG. 5]
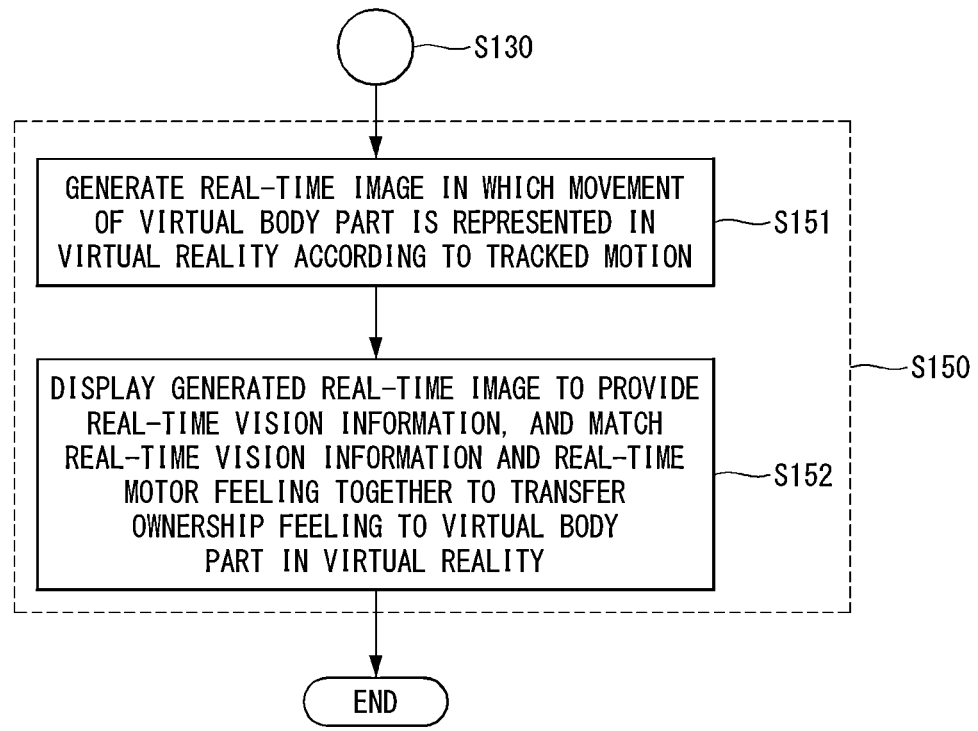

[FIG. 6]
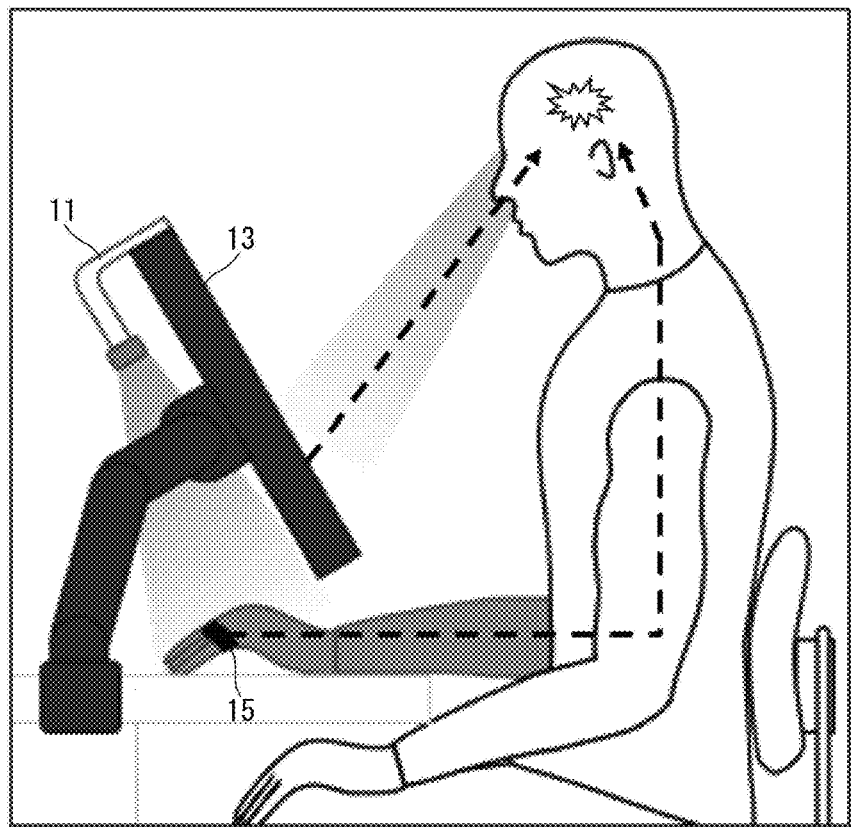
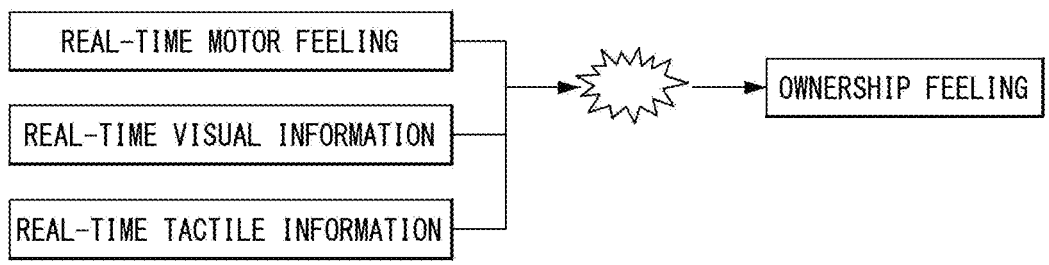

[FIG. 7]
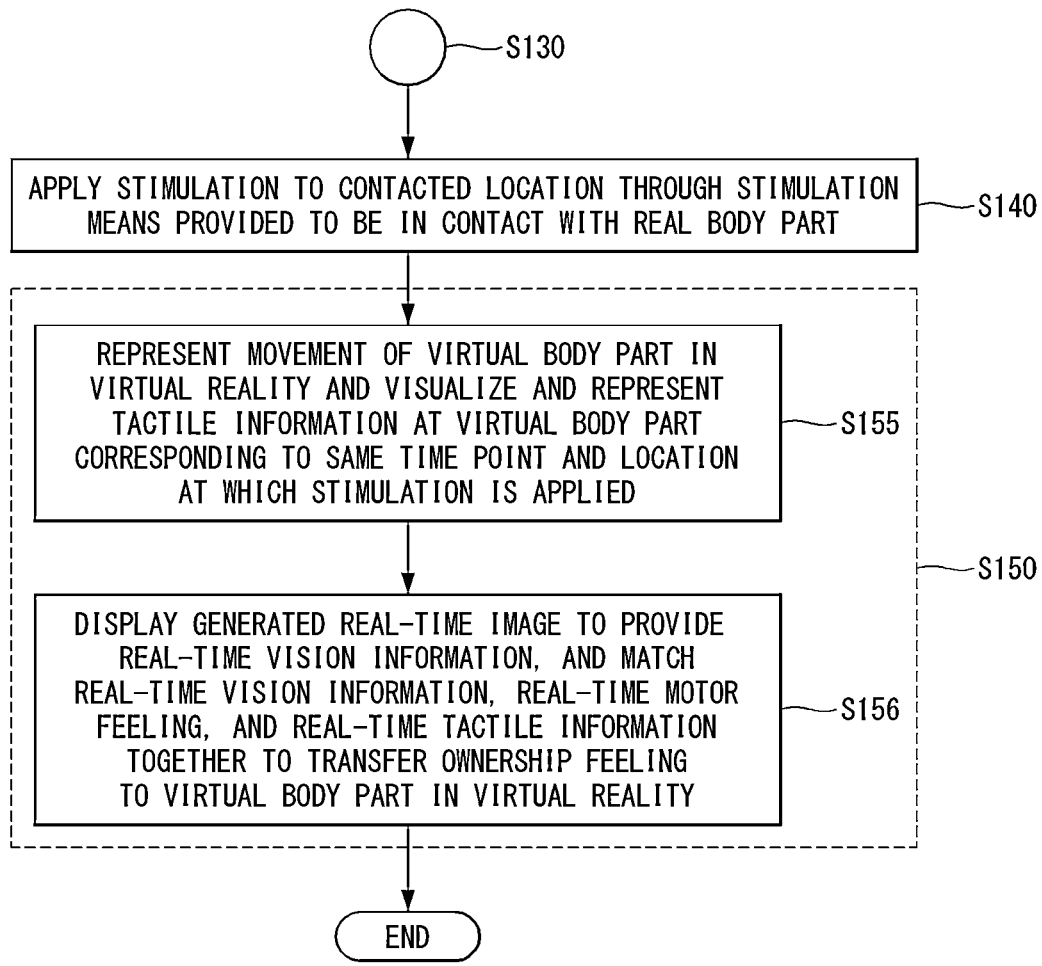

[FIG. 8]
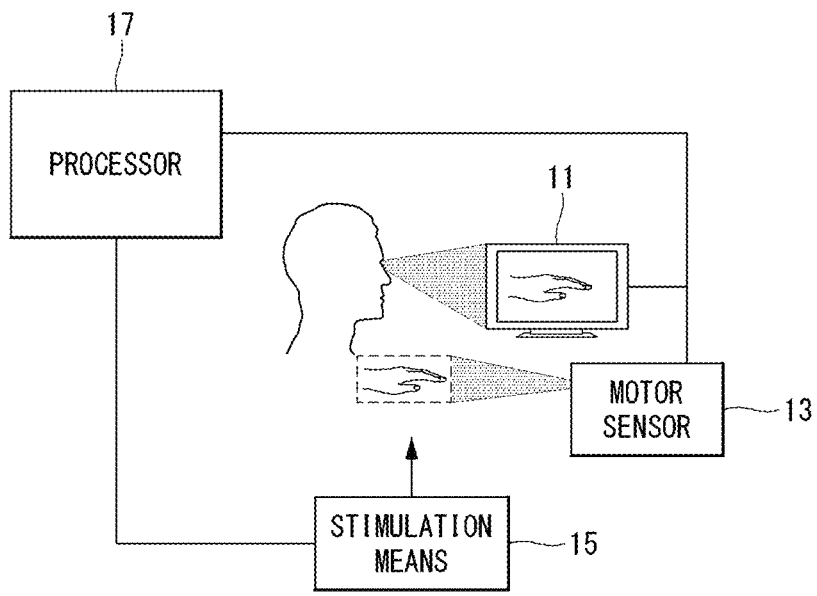
[FIG. 9]
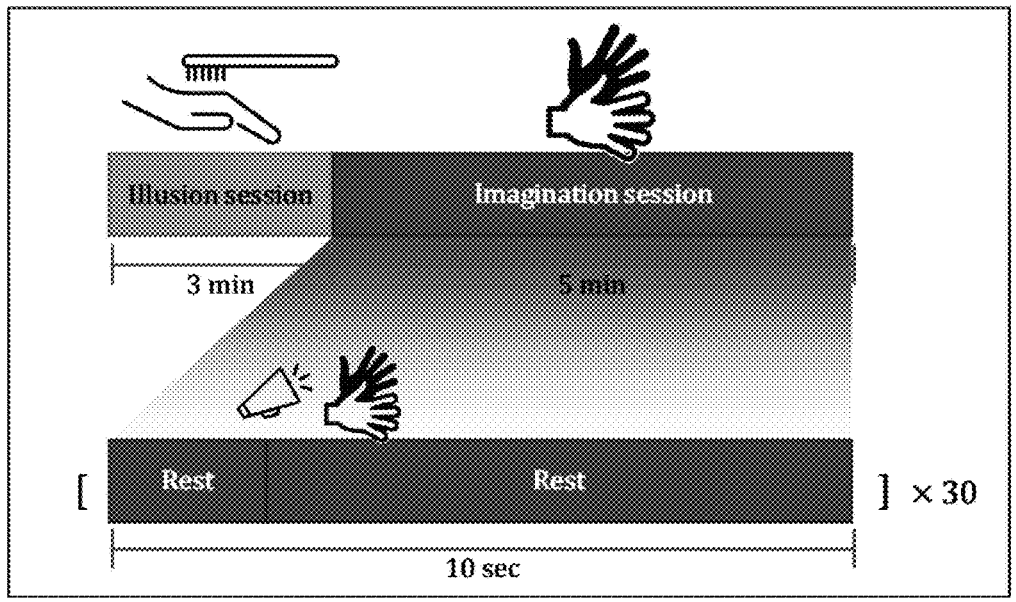

[FIG. 10]
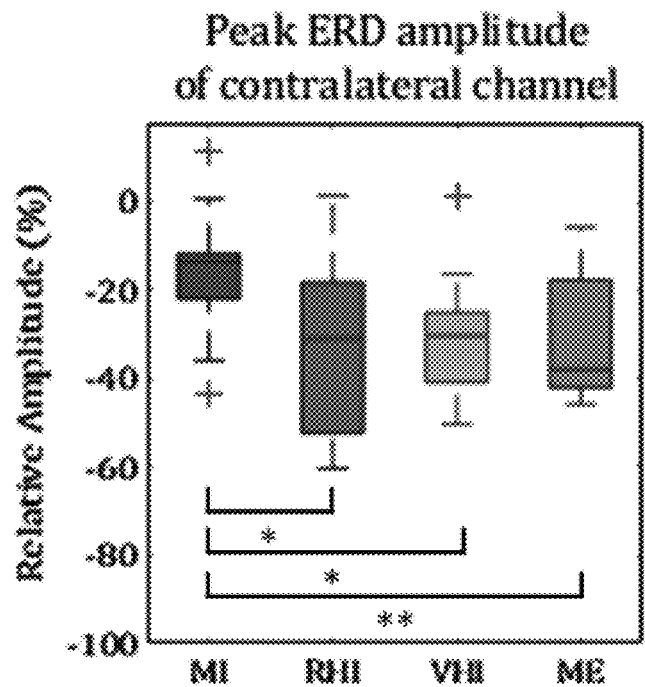
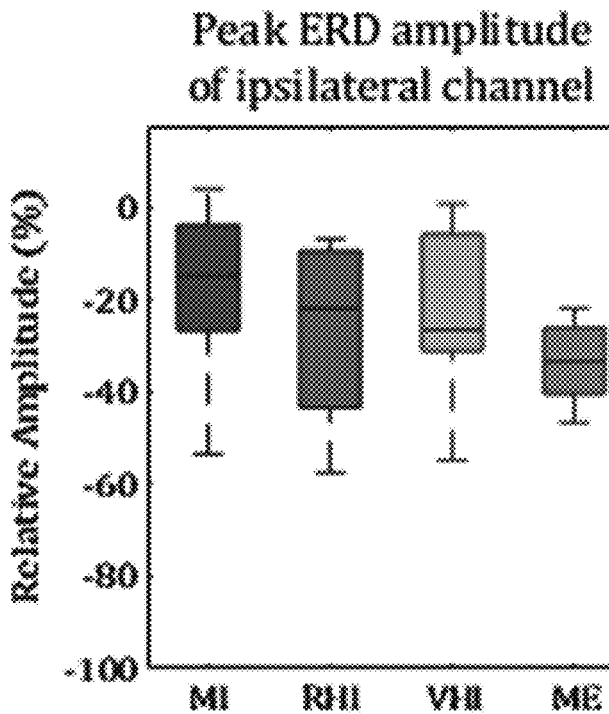

[FIG. 11]
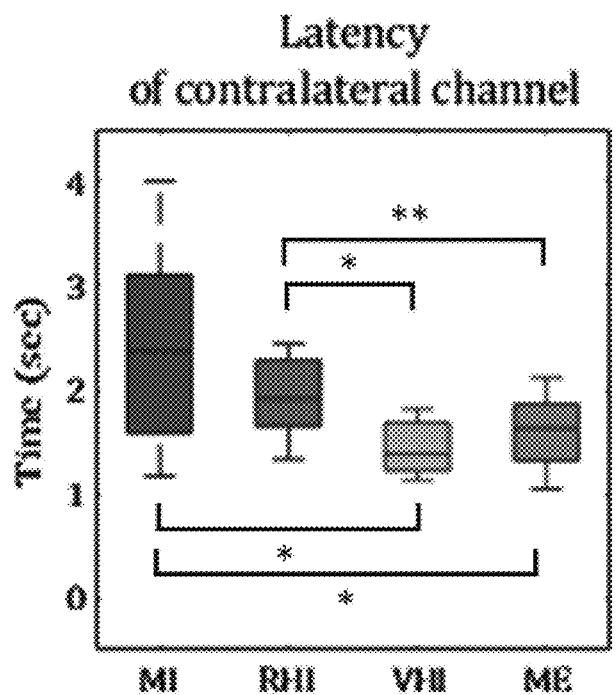
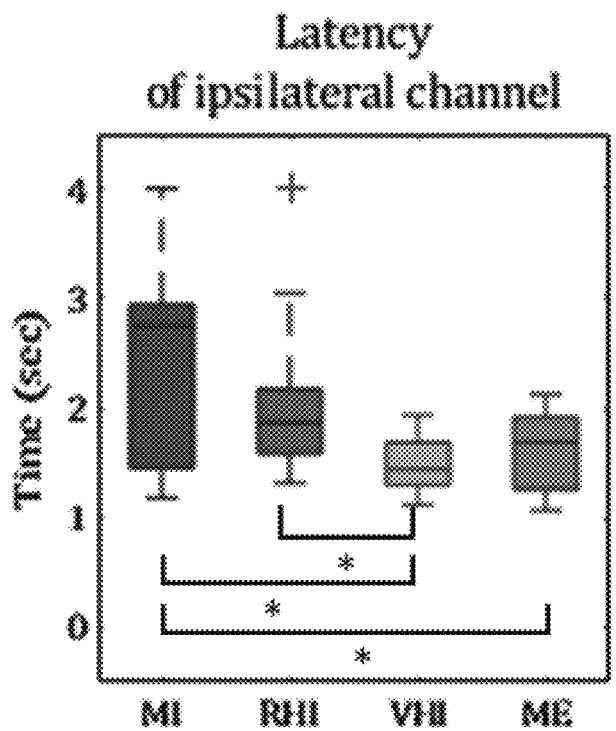

GUIDANCE METHOD FOR MOTOR IMAGERY AND APPARATUS THEREOF

CROSS-REFERENCE TO RELATED APPLICATIONS

This application claims the benefit under 35 USC 119(a) of Korean Patent Application No. 10-2021-0123105 filed on Sep. 15, 2021, in the Korean Intellectual Property Office, the entire disclosure of which is incorporated herein by reference for all purposes.

BACKGROUND OF THE DISCLOSURE

Field of the Disclosure

The present disclosure relates to a technique that trains humans to reinforce brain waves, and more particular, to a guidance method and apparatus for motor imagery that are utilized as an input signal for brain-computer interface (BCI) or utilized in rehabilitation of patients to restore motor skills.

Related Art

Motor imagery has been widely used to generate an input signal for brain-computer interface (BCI). The BCI is an interface for communication between humans and machines, and is a means to control a machine without physical input such as a keyboard or touch screen using human brain wave signals, for example, electroencephalogram (EEG). Therefore, efforts are continuously being made to interpret brain waves to understand its meaning, and among these brain wave signals, the motor imagery signal is used to identify an action or intention that a human intends to perform.

Meanwhile, the motor imagery is also used as an evaluation index for motor skill in stroke patients. In the field of rehabilitation medicine or sports science, motor imagery training is being conducted as a means to recover or improve human motor skills. That is, real body functions are improved through motor imagery training. The related art literature presented below introduces clinical results showing that physical ability of stroke patients may be recovered through the motor imagery training.

The motor imagery-based BCI has characteristics similar to a human plan-execution process. Despite the usefulness of such motor imagery-based BCI, a task of the motor imagery may come to users as an ambiguous task, and there is a characteristic of generating weaker cortical signals compared to performing a direct exercise. Therefore, many efforts to reinforce the motor imagery are continuously being studied.

RELATED ART DOCUMENT

Non-Patent Document

"Imagery Training Effects of Upper Limb Function and Activities of Daily Living in Subacute Stroke Patients," Journal of Digital Convergence, 2013, vol. 11, no. 8, pp. 235-242

SUMMARY OF THE DISCLOSURE

The present disclosure is to overcome a limitation that motor imagery signals utilized in brain-computer interfaces (BCI) generate weak cortical signals due to their ambiguity, and solve a weakness that the conventional training methods for enhancing motor imagery do not lead a user to complete immersion because the conventional training methods for reinforcing motor imagery provides only visual guidance.

In an aspect, a guidance method for motor imagery may include: displaying, by a guidance apparatus for motor imagery, virtual reality including a virtual body part corresponding to a user's real body part to the user; detecting and tracking, by the guidance apparatus for motor imagery, a movement of the real body part through a motion sensor; and visually displaying, by the guidance apparatus for motor imagery, the movement of the virtual body part through the virtual reality according to the tracked motion to induce an ownership feeling that makes the user mistake the virtual body part for the real body part.

The inducing of the ownership feeling may include: generating a real-time image representing the movement of the virtual body part in the virtual reality according to the tracked motion; and providing real-time visual information to the user by displaying the generated real-time image through a display means, and matching the real-time visual information and a real-time motor feeling in which the user moves the real body part together to transfer the ownership feeling to the virtual body part in the virtual reality.

The guidance method may further include: applying, by the guidance apparatus for motor imagery, stimulation to a contacted location through at least one stimulation means provided to be in contact the real body part, in which the inducing of the ownership feeling may include: representing the movement of the virtual body part in the virtual reality according to the tracked motion and generating a real-time image visualizing and representing tactile information on the virtual body part corresponding to the same time point and location at which the stimulation is applied through the stimulation means; and providing real-time visual information to the user by displaying the generated real-time image through a display means and matching the real-time visual information and a real-time motor feeling in which the user moves the real body part, and the real-time tactile information recognized through the real body part together to transfer the ownership feeling to the virtual body part in the virtual reality.

Hereinafter, there is provided a computer-readable recording medium in which a program for a computer to execute the method described above is recorded.

In another aspect, a guidance apparatus for motor imagery may include: a display means configured to display an image; a motion sensor configured to detect a movement of a body part; and a processor configured to drive a program to guide motor imagery, in which the program driven by the processor may include an instruction that displays virtual reality including a virtual body part corresponding to a user's real body part to the user through the display means, detects the movement of the real body part through the motion sensor to track a motion, and visually displays the movement of the virtual body part through the virtual reality according to the tracked motion to induce an ownership feeling that makes the user mistake the virtual body part for a real body part.

The program driven by the processor may include an instruction that generates a real-time image representing the movement of the virtual body part in the virtual reality according to the tracked motion, provide real-time visual information to the user by displaying the generated real-time image through a display means and match the real-time visual information and a real-time motor feeling in which the user moves the real body part together to transfer the ownership feeling to the virtual body part in the virtual reality.

The guidance apparatus may further include: at least one stimulation means configured to be in contact with the real body part to apply stimulation to the contacted location, in which the program driven by the processor may include an instruction that represents the movement of the virtual body part in the virtual reality according to the tracked motion, generates a real-time image visualizing and representing tactile information on the virtual body part corresponding to the same time point and location at which the stimulation is applied through the stimulation means, and provides real-time visual information to the user by displaying the generated real-time image through a display means and matches the real-time visual information and a real-time motor feeling in which the user moves the real body part, and the real-time tactile information recognized through the real body part together to transfer the ownership feeling to the virtual body part in the virtual reality.

BRIEF DESCRIPTION OF THE DRAWINGS

FIG. 1 is a diagram for describing a "rubber hand illusion" phenomenon in which a fake hand is mistaken for a real hand.

FIG. 2 is a diagram for describing a mechanism for giving an ownership feeling to a user by using a guidance apparatus for motor imagery proposed by an embodiment of the present disclosure.

FIG. 3 is a flowchart of a guidance method for motor imagery according to an embodiment of the present disclosure.

FIG. 4 is a flowchart illustrating in more detail a process of displaying virtual reality to a user in the guidance method for motor imagery of FIG. 3 according to an embodiment of the present disclosure.

FIG. 5 is a flowchart illustrating in more detail a process of inducing an ownership feeling in the guidance method for motor imagery of FIG. 3 according to the embodiment of the present disclosure.

FIG. 6 is a diagram for describing a mechanism for giving an ownership feeling to a user by adding a stimulation means to the guidance apparatus for motor imagery of FIG. 2.

FIG. 7 is a flowchart illustrating in more detail a process of inducing an ownership feeling by additionally utilizing the simulation means in the guidance method for motor imagery of FIG. 2 according to the embodiment of the present disclosure.

FIG. 8 is a block diagram illustrating the guidance apparatus for motor imagery according to the embodiment of the present disclosure.

FIG. 9 is a diagram for describing a verification experiment implementing a motor imagery guidance technology according to embodiments of the present disclosure.

FIGS. 10 and 11 are diagrams illustrating results according to the verification experiment of FIG. 9.

DESCRIPTION OF EXEMPLARY EMBODIMENTS

Hereinafter, embodiments of the present disclosure will be described in detail with reference to the drawings. However, detailed descriptions of known functions or configurations that may obscure the gist of the present disclosure in the following description and accompanying drawings will be omitted. Furthermore, throughout the present specification, unless explicitly described to the contrary, "including" any components will be understood to imply the inclusion of other elements rather than the exclusion of any other elements.

The terms used in the present disclosure are only used to describe specific embodiments, and are not intended to limit the present disclosure. Singular forms are intended to include plural forms unless the context clearly indicates otherwise. It will be further understood that the terms "includes" or "comprises" used in this specification, specify the presence of stated features, steps, operations, components, parts, or a combination thereof, but do not preclude the presence or addition of one or more other features, numerals, steps, operations, components, parts, or a combination thereof.

Unless indicated otherwise, it is to be understood that all the terms used in the specification including technical and scientific terms have the same meaning as those that are generally understood by those who skilled in the art. It must be understood that the terms defined by the dictionary are identical with the meanings within the context of the related art, and they should not be ideally or excessively formally defined unless the context clearly dictates otherwise.

FIG. 1 is a diagram for describing a "rubber hand illusion" phenomenon in which a fake hand is mistaken for a real hand.

Referring to FIG. 1, subject's real hands (real hands) are placed on a desk, and rubber hands (fake hands) similar to the real hands are placed side by side. In this case, the subject is covered with a screen or the like to prevent the subject from seeing his/her hands. Now, starting the experiment, an experimenter uses a brush to simultaneously sweep both the real hand and the rubber hand with the brush. In this case, since the real hand and the rubber hand are swept at the same time point, the subject feels the touch of the brush through the real hand while seeing the brush touching the rubber hand. When the above process is repeatedly performed for a certain period of time, a phenomenon in which the subject mistakes the visually recognized rubber hand for their real hand appears. Therefore, even if the appearance of brushing only the rubber hand without brushing the real hand beyond the screen is visually recognized at some point, the subject falls into the illusion of feeling (tactile sensation) the touch of the brush.

The phenomenon of mistaking other objects for a part of his/her body is called "rubber hand illusion." This illusion is a confusion caused by human sensory and mental processes, and is a phenomenon in which, by synthesizing sensory information, the brain believes that what the brain thinks exists is real. In other words, even if there is no tactile sensation, when the brain believes that brushstrokes are being made by synthesizing various pieces of sensory information such as visual information, the brain will mistakenly think that the tactile sensation exists.

Researchers have found that a premotor cortex is activated when the rubber hand illusion occurs. The three sensations that the human body feels are: vision, tactile sensation, and proprioceptive sensation (proprioception). The premotor cortex is a region that receives and integrates information from these sensations to form a sensation called "my body." However, since the power of vision is often strong, the illusion that the brain is deceived by seeing appears even if the other sensations are working properly.

The embodiments of the present disclosure presented below intend to propose a technique for training motor imagery by borrowing the principle of this "rubber hand illusion." However, there is a possibility of weakening the subject's immersion because there is a limit or gap in directly manufacturing a physical device such as a rubber hand and reproducing the user's movement through the rubber hand. Therefore, the embodiments of the present disclosure presented below intend to induce quick and easy immersion of the user by more conveniently realizing the user's real body, but simultaneously simulating the user's real body instead of physical hardware with constraints such as the rubber hands.

FIG. 2 is a diagram for describing a mechanism for giving an ownership feeling to a user by using a guidance apparatus for motor imagery proposed by an embodiment of the present disclosure. Here, the ownership feeling refers to a sensation that makes a human mistake a virtual object for a real body part. As described above, in FIG. 1, a fake body part such as the rubber hand was exemplified as a virtual object, but an object in which a virtual image or shape made with graphics is somewhat different from that of a human hand may also be utilized as a virtual object. The important point is that the stronger the degree of inducing immersion by deceiving the human sensations, the higher the probability of falling into the rubber hand illusion.

Referring to FIG. 2, a motion sensor 11 for capturing the movement of the user's real hand is provided to track the specific movement of the finger as well as the movement of the hand. The movement information is acquired through the motion sensor 11 and displayed in real time through a display means 13. That is, the movement of the user's real hand is provided to the user by being imaged in real time. In this case, the user's real hand may be completely shielded from the user's field of view by being covered by the display means 13. Through this visual separation, the user perceives the movement of the virtual hand displayed only through the display means 13. For the immersion, the virtual hand displayed on the display means 13 may be displayed in a kind of virtual reality, and move in real time by reflecting the movement of the user's real hand as it is. Accordingly, two major inputs are provided to the user's brain. The first is a real-time motor feeling of the real hand moving by the user, and the second is real-time visual information displayed on the display means 13 and recognized through user's eyes. These two inputs interact through the user's brain to match the stimulation, thereby providing the user with the ownership feeling that makes the user mistake the virtual hand displayed on the display means 13 as if the virtual hand is his/her real hand to cause the virtual hand illusion (VHI) phenomenon. That is, FIG. 2 may be implemented as a VHI (visuomotor information based (VHI, VM-VHI) guidance system using visuo-motion information.

FIG. 3 is a flowchart illustrating a guidance method for motor imagery according to an embodiment of the present disclosure, and a series of processing processes by the guidance apparatus for motor imagery including the motion sensor 11 and the display means 13 illustrated in FIG. 2 is presented.

In step S110, the guidance apparatus for motor imagery displays virtual reality including a virtual body part corresponding to a user's real body part to the user. In this case, the virtual reality is provided to give visual immersion while preventing a user from seeing his/her real body part. Therefore, it should at least be advantageous for real-time motion simulation compared to a physical device replacing a real body part. That is, the user should be able to quickly and accurately simulate the situation in which the user moves his/her body part. However, the virtual reality does not necessarily have to implement the same or different virtual world as the graphic. In addition, the virtual body part displayed in the virtual reality may be an image implemented similar to a real hand or may be implemented as a hand having a shape different from that of the real hand. For example, by replacing a real hand placed on a desk, a virtual hand may be implemented with a hand of a monkey sitting on a tree or a hand of a robot working in a factory, and by modeling a real desk and a real hand, it may be possible to implement a virtual hand placed on the virtual desk as an image.

Referring to FIG. 4 illustrating this process (S110) in more detail, in step S111, a real body part located so as not to be seen from a user's vision and a virtual body part corresponding to the real body part are mapped, and the virtual body part is included in the virtual reality to generate an image. As described above, in the embodiments of the present disclosure, since it is necessary to induce the illusion as if the tactile sensation is real through visual information, the real hand is completely shielded from the user's field of view to promote the immersion. To this end, the real hand may be accommodated in a separate device, a shielding film covering the real hand may be used, or the user's field of view may be completely covered by the display means. Then, in step S112, the previously generated image may be displayed through the display means located to face the user's vision. Therefore, the display means should be formed to at least have a structure or size that may cover the real hand, and may be implemented as a head mounted display (HMD) that may completely cover a user's field of view if necessary.

Referring back to FIG. 3, in step S130, the guidance apparatus for motor imagery detects the movement of the real body part through the motion sensor and tracks the motion. In this case, it is preferable to perform the detection of the movement and the tracking of the motion in real time. This is because, when the detected/tracked information is visually represented later, the visualized information needs to be displayed simultaneously with the motor feeling of the user's real body part.

In step S150, the guidance apparatus for motor imagery visually displays the movement of the virtual body part through the virtual reality according to the tracked motion to induce the ownership feeling that makes the user mistake the virtual body part for the real body part. In this process, the user matches the visual information and the motor feeling (motor motion information) while performing a reaching motion toward the goal presented in the virtual reality. In order to cause the virtual hand illusion, the motor feeling through the user's real body part and the visual stimulation displayed through the display means are integrated through the brain. When this stimulation is given for a certain period of time or intensity, the human brain begins to mistake the virtual body part shown through the visual stimulation as if the virtual body part is his/her real body part.

Referring to FIG. 5 illustrating this process (S150) in more detail, in step S151, a real-time image representing the movement of the virtual body part in the virtual reality is generated according to the motion tracked in step S130. In order to cause the virtual hand illusion, the real-time image represented in the virtual reality needs to be visualized so that the same part as the movement of the user's real body part moves at the same time point. Furthermore, in order to induce the quick and strong immersion of the user, a region in which the movement is represented in the real body part according to the tracked motion may be visually highlighted and displayed in the same region in the virtual body part. For example, when the user is moving an index finger in the user's real hand, a region corresponding to the index finger among the virtual body parts represented in the virtual reality is highlighted and displayed with a different color or brightness simultaneously with the movement at the same time point, so the user may visually strongly stimulate the movement of the same virtual body part as his/her real body part.

Then, in step S152, the real-time visual information may be provided to the user by displaying the generated real-time image through the display means, and the real-time visual information and the real-time motor feeling in which the user moves the real body part are matched together to transfer the ownership feeling to the virtual body part in the virtual reality. That is, the user's brain integrates the motor feeling and the visualized information through his/her body to match the stimulation to reach the ownership feeling which mistakes the virtual body part displayed through the display means for his/her body part.

Meanwhile, in step S152, for the complete immersion, the provision of the real-time visual information and the real-time motor feeling to the user over a preset reference time or reference intensity may simultaneously continue so that the user may reach the level of the ownership feeling. In the viewpoint of implementation, the preset reference time or the reference intensity may be set so that the electroencephalogram (EEG) signal measured from the user is equal to or greater than a threshold value. Since there may be individual differences in the level at which the user falls into illusion when the user reaches immersion, the average intensity standard, the minimum time standard for immersion, or the like may be prepared from data experimentally accumulated through a large number of subjects.

Furthermore, after the guidance apparatus for motor imagery induces the ownership feeling to the user, the guidance apparatus for motor imagery may further perform a process of controlling the real body part not to move but displaying an image in which the virtual body part performs a preset target movement in the virtual reality to the user to induce the motor imagery. The process is based on the assumption that the illusion has reached a certain level, and only by observing the movement of the virtual body part, the training effect of further reinforcing the user's brain wave (motor imagery) is shown. In other words, it helps the user's motor imagery by inducing an experience as if his/her real body part is performing a target movement just by observing the visual stimulation.

FIG. 6 is a diagram for describing a mechanism for giving an ownership feeling to a user by adding a stimulation means to the guidance apparatus for motor imagery of FIG. 2. The motion sensor 11 for capturing the movement of the user's real hand and the display means 13 for displaying the acquired real-time movement information are the same as described above with reference to FIG. 2. FIG. 6 further includes a stimulation means 15 in addition to these components. The stimulation means 15 may contact the user's real body part and apply the stimulation to the corresponding location, and a plurality of stimulation means 15 may be attached to a small region of a body part to be moved. In this case, the stimulation may be selectively applied only to the small region that moves according to the movement of the corresponding part. For example, the stimulation means is attached to each finger of the user, and when the user moves a thumb, stimulation such as vibration may be applied through the stimulation means attached to the thumb. In addition, a visualized mark may be displayed at the same time point as the stimulation application time point on the virtual body part corresponding to the same location as the stimulation applied through the stimulation means 15. That is, by displaying the stimulation at the same time point and location on the real body part and the virtual body part, the virtualization of the tactile information is promoted.

Accordingly, unlike the case of FIG. 2, in FIG. 6, three major inputs are given to the user's brain. The first is the real-time motor feeling of the real hand moving by the user himself, the second is the real-time visual information displayed on the display means 13 and perceived through the user's eyes, and the third is the real-time tactile information detected by the stimulation means 15. These two inputs interact through the user's brain to match the stimulation, thereby providing the user with the ownership feeling that makes the user mistake the virtual hand displayed on the display means 13 as if the virtual hand is his/her real hand to cause the virtual hand illusion (VHI) phenomenon. That is, FIG. 6 may be implemented as a VHI (visuo-tactile information based VHI, VT-VHI) guidance system using visuo-tactile information.

FIG. 7 is a flowchart illustrating a process of inducing the ownership feeling by additionally using the stimulation means in the guidance method for motor imagery of FIG. 2 according to an embodiment of the present disclosure, and illustrates a process continuously performed to a step (S130) of detecting the movement of the real body part through the motion sensor and tracking the motion.

In step S140, the guidance apparatus for motor imagery applies the stimulation to the contacted location through at least one stimulation means provided to be in contact with the real body part. This process is provided to add the tactile sensation stimulation in addition to the visual stimulation or the motor feeling described above, and is to induce stronger immersion. In particular, as feedback on the movement of the user's real body part, the stimulation may be selectively applied only to the stimulation means attached to the corresponding part according to the movement. To this end, the stimulation may be applied to the real body part at different time points and locations through the plurality of stimulation means. This stimulation means may be implemented as a vibration motor to provide immediate stimulation to the attached location.

Now, the process proceeds to the step of inducing the ownership feeling (S150).

In step S155, the movement of the virtual body part may be represented in the virtual reality according to the tracked motion through step S130, and the real-time image visualizing and representing the tactile information on the virtual body part corresponding to the same time point and location at which the stimulation is applied through the stimulation means may be generated. When the stimulation is applied to the real body part at different time points and locations through the plurality of stimulation means in step S140, in step S155, by representing the tactile information visualized in the contact region of the virtual body part in real time in response to the stimulation applied at different time points and locations through the plurality of stimulation means, it is possible to induce stronger immersion. Alternatively, when the stimulation was applied only to small parts moving according to the user's movement in step S140, in step S155, separately highlighted visual stimulation (for example, color, brightness, or the like may be changed to display, or separate indicator lights attached to each small part of the virtual body part may be turned on) may be displayed in real time in response to the moving small part of the virtual body part.

In step S156, by displaying the generated real-time image through the display means to provide the real-time visual information to the user by and matching the real-time visual information and the real-time motor feeling in which the user moves the real body part, and the real-time tactile information recognized through the real body part together, it is possible to transfer the ownership feeling to the virtual body part in the virtual reality. That is, the user's brain integrates the motor feeling, the visualized information, and the tactile information through his/her body to match the stimulation to reach the ownership feeling which mistakes the virtual body part displayed through the display means for his/her body part.

FIG. 8 is a block diagram illustrating the guidance apparatus for motor imagery according to the embodiment of the present disclosure, in which the time-series process described in FIG. 3 is reconstructed from the viewpoint of hardware. Therefore, in order to avoid a duplication of description, here, only the outline of each configuration will be outlined, focusing on the function and motion of the apparatus.

The display means 11 is a component for displaying an image, and is located to face the user's vision, and may be configured as either a display device or a head mounted display (HMD) formed so that the real body part is not be seen from the user's vision.

The motion sensor 13 is configured to detect the movement of the real body part and transmits the movement detected in real time to the processor 17, so the corresponding virtual movement or visual stimulation may be displayed through the display means 11.

The processor 17 is configured to drive a program guiding the motor imagery, and the program driven by the processor includes an instruction that displays virtual reality including a virtual body part corresponding to a user's real body part to the user through the display means 11, detects the movement of the real body part through the motion sensor 13 to track a motion, and visually displays the movement of the virtual body part through the virtual reality according to the tracked motion to induce an ownership feeling that makes the user mistake the virtual body part for a real body part. The program driven by the processor 17 may include an instruction that maps the real body part located so as not to be seen from a user's vision to the virtual body part corresponding to the real body part and generates an image by including the virtual body part in the virtual reality, and displays the generated image through the display means 11 located to face the user's vision.

The program driven by the processor 17 may include an instruction that generates a real-time image representing the movement of the virtual body part in the virtual reality according to the tracked motion, provides real-time visual information to the user by displaying the generated real-time image through the display means 11, matches the real-time visual information and a real-time motor feeling in which the user moves the real body part together to transfer the ownership feeling to the virtual body part in the virtual reality. In addition, the program driven by the processor 17 may visually highlight and display the region in which the movement is represented in the real body part according to the tracked motion in the same region in the virtual body part to generate the real-time image.

Furthermore, the program driven by the processor 17 may simultaneously continue to provide the real-time visual information and the real-time motor feeling to the user over a preset reference time or reference intensity so that the user reaches a level of the ownership feeling to transfer the ownership feeling. To this end, the preset reference time or the reference intensity may be set so that the electroencephalogram (EEG) signal measured from the user is equal to or greater than a threshold value.

Meanwhile, the guidance apparatus for motor imagery of FIG. 8 may further include at least one stimulation means 15 for applying the stimulation to the contacted location by contacting the real body part. In this case, the program driven by the processor 17 may include an instruction that represents the movement of the virtual body part in the virtual reality according to the tracked motion, generates a real-time image visualizing and representing tactile information on the virtual body part corresponding to the same time point and location at which the stimulation is applied through the stimulation means, and provides real-time visual information to the user by displaying the generated real-time image through the display means 11 and matches the real-time visual information and a real-time motor feeling in which the user moves the real body part, and the real-time tactile information recognized through the real body part together to transfer the ownership feeling to the virtual body part in the virtual reality.

In addition, the plurality of stimulation means 15 may be provided to apply the stimulation to the real body part at different time points and locations. In this case, the program driven by the processor 17 may represent the tactile information visualized in the contact region of the virtual body part in real time in response to the stimulation applied at different time points and locations through the plurality of stimulation means to induce the ownership feeling.

In this case, the program driven by the processor 17 may further include an instruction that induces the ownership feeling to the user, and then controls the real body part not to move, but displays an image in which the virtual body part performs a preset target movement in the virtual reality to the user to induce the motor imagery.

FIG. 9 is a diagram for describing a verification experiment implementing a motor imagery guidance technology according to embodiments of the present disclosure. Hereinabove, by implementing the guidance apparatus for motor imagery suggested by the embodiments of the present disclosure, an experiment was conducted to confirm how effectively the guidance of the motor imagery is occurring and how the motor imagery signal is improved through this. To this end, after an illusion session for inducing the user's ownership feeling to the virtual body part in the virtual reality is first performed, it is observed that the virtual body part to which the ownership feeling is given performs the target movement through the "illusion session," the imagination session helping the user's motor imagery is performed according to the time and the number of repetitions illustrated in FIG. 9.

The motor imagery signal was measured using an electroencephalogram (EEG) device, and the intensity of the motor imagery signal was verified for normal persons. In this comparative verification experiment, the degree of reinforcement of the motor imagery was compared with respect to the guidance system for motor imagery according to the embodiment of the present disclosure using the virtual reality and the guidance system for motor imagery using the physical rubber hand. As the control group, by comparing the case of performing pure motor imagery without any device with the case of the real motor performance together, the technique suggested by the embodiments of the present disclosure evaluated how much motor imagery is reinforced and compared how similar performance is shown when compared to the case of the real motor performance. In the experiment, a total of four paradigms of the pure motor imagery (denoted as "MI"), the guidance system for motor imagery (denoted as "RHI") using the physical rubber hand illusion phenomenon, the guide system for motor imagery (denoted as "VHI") using the virtual hand illusion phenomenon suggested by the embodiments of the present disclosure, and the real motor performance (denoted as "ME") were compared.

FIGS. 10 and 11 are diagrams illustrating results according to the verification experiment of FIG. 9. FIG. 10 is a contralateral region result (C3 region) of the comparative verification experiment, and FIG. 11 is an ipsilateral region result (C4 region) of the comparative verification experiment. Experimental results were measured through the EEG signals, and event-related desynchronization (ERD) signals represented during the motor task were measured and compared from the EEG signals. The motor task performed a hand extension/grasping motion, and the intensity in the C3 region, known as a source of ERD was compared when a normal person performed the hand motion operation.

As a result of the comparative verification experiment, the guidance system for motor imagery using the VHI suggested by the embodiments of the present disclosure showed higher motor imagery signal reinforcement in both the ipsilateral region and the contralateral region compared to the pure motor imagery that did not use the VHI. Comprehensively considering the signal reinforcement and delay, it could be confirmed that the guidance system was similar to the motor performance and showed similar or superior performance to the RHI-based guide system for motor imagery using the physical rubber hand. In particular, considering the aspect that the guidance system for motor imagery using the VHI according to the embodiments of the present disclosure is relatively free from physical constraints and easy to expand functionally, it can be seen that the system is more advantageous than the RHI-based guidance system for motor imagery in terms of application and usability as well as the degree of motor reinforcement.

According to the above-described embodiments of the present disclosure, by matching the real-time motor feeling with the real-time visual information through the virtual reality image about the virtual body part generated from the movement information obtained from the movement of the real body part, it is possible to more easily guide the ambiguous task of the motor imagery to the user, by generating the brain wave signal of the reinforced motor imagery due to the ownership feeling induced by the user's strong immersion, it is advantageous for the feature extraction through the brain wave analysis or the application of the BCI application system based on the motor imagery, and by simulating the user's motion through the virtual reality rather than moving the real device, it has the advantage of being free from the physical constraints as well as being free of the functional extension or utilization. Furthermore, by matching the motor feeling (motor motion information) with the visual stimulation in addition to the tactile information that may be selectively used in the process of inducing the ownership feeling, the individual physical characteristics are more free than when only the tactile information is used. For example, since it is difficult to use the tactile information in patients who have paralysis in a part of the body or are lack of the tactile information, it is possible to guide the motor imagery by visualizing the motor feeling (motor motion information) to induce the ownership feeling.

Meanwhile, the embodiments of the present disclosure can be implemented as computer-readable codes on a computer-readable recording medium. The computer-readable recording medium includes all kinds of recording apparatuses in which data that may be read by a computer system are stored.

An example of the computer readable recording medium may include a read only memory (ROM), a random access memory (RAM), a compact disk read only memory (CD-ROM), a magnetic tape, a floppy disk, an optical data storage, or the like. In addition, the computer readable recording medium may be distributed in computer systems connected to each other through a network, such that the computer readable codes may be stored in a distributed scheme and executed. In addition, functional programs, codes, and code segments for implementing the present disclosure can be easily inferred by programmers in the technical field to which the present disclosure belongs.

Embodiments of the present disclosure can more easily guide an ambiguous task of motor imagery to a user, can be advantageously applied to feature extraction through brain wave analysis and application of a BCI application system due to reinforced motor imagery, can not only simulate a motion free from physical constraints, but also freely expand or utilize functions through virtual reality, and can guide motor imagery to patients who have difficulty in using tactile information by visualizing motor feeling (motor motion information).

Hereinabove, the present disclosure has been described with reference to various embodiments. Those of ordinary skill in the technical field belonging to the present disclosure will be able to understand that the present disclosure can be implemented in modified forms without departing from the essential characteristics of the present disclosure. Therefore, embodiments disclosed herein should be considered in an illustrative aspect rather than a restrictive aspect. The scope of the present invention should be defined by the claims rather than the above-mentioned description, and equivalents to the claims should be interpreted to fall within the present invention.

What is claimed is:

1. A guidance method for motor imagery, comprising:
    displaying, by a guidance apparatus for motor imagery, virtual reality including a virtual body part corresponding to a user's real body part to the user;
    detecting and tracking, by the guidance apparatus for motor imagery, a movement of the real body part through a motion sensor;
    applying, by the guidance apparatus for motor imagery, tactile stimulation to a contacted location through a stimulation means provided to be in contact with the real body part;
    visually displaying, by the guidance apparatus for motor imagery, the movement of the virtual body part through the virtual reality according to the tracked motion and tactile information from the stimulation means to induce an ownership feeling that makes the user mistake the virtual body part for the real body part; and
    after the inducing, by the guidance apparatus for motor imagery, of the ownership feeling to the user, controlling the real body part not to move but displaying an image in which the virtual body part performs a preset target movement in the virtual reality to the user to induce the motor imagery.

2. The guidance method of claim 1, wherein the displaying of the virtual reality to the user includes:
    mapping the real body part located so as not to be seen from a user's vision to the virtual body part corresponding to the real body part and generating an image by including the virtual body part in the virtual reality; and displaying the generated image through a display means located to face the user's vision.

3. The guidance method of claim 1, wherein the inducing of the ownership feeling includes:
generating a real-time image representing the movement of the virtual body part in the virtual reality according to the tracked motion; and
providing real-time visual information to the user by displaying the generated real-time image through a display means, and matching the real-time visual information and a real-time motor feeling in which the user moves the real body part together to transfer the ownership feeling to the virtual body part in the virtual reality.

4. The guidance method of claim 3, wherein, in the generating of the real-time image, a region in which the movement is represented in the real body part according to the tracked motion is visually highlighted and displayed in the same region in the virtual body part.

5. The guidance method of claim 3, wherein, in the transferring of the ownership feeling, the provision of the real-time visual information and the real-time motor feeling to the user over a preset reference time or reference intensity simultaneously continues so that the user reaches a level of the ownership feeling.

6. The guidance method of claim 5, wherein the preset reference time or the reference intensity is set so that an electroencephalogram (EEG) signal measured from the user is equal to or greater than a threshold value.

7. The guidance method of claim 1,
wherein the inducing of the ownership feeling includes:
representing the movement of the virtual body part in the virtual reality according to the tracked motion and generating a real-time image visualizing and representing the tactile information on the virtual body part corresponding to the same time point and location at which the tactile stimulation is applied through the stimulation means; and
providing real-time visual information to the user by displaying the generated real-time image through a display means and matching the real-time visual information and a real-time motor feeling in which the user moves the real body part, and the real-time tactile information recognized through the real body part together to transfer the ownership feeling to the virtual body part in the virtual reality.

8. The guidance method of claim 7, wherein, in the applying of the stimulation, the stimulation is applied to the real body part at different time points and locations through a plurality of stimulation means, and
in the inducing of the ownership feeling, the tactile information visualized in the contact region of the virtual body part is represented in real time in response to the stimulation applied at different time points and locations through the plurality of stimulation means.

9. A guidance apparatus for motor imagery, comprising:
a display means configured to display an image;
a motion sensor configured to detect a movement of a body part; and
a processor configured to drive a program to guide motor imagery,
wherein the program driven by the processor includes an instruction that displays virtual reality including a virtual body part corresponding to a user's real body part to the user through the display means, detects the movement of the real body part through the motion sensor to track a motion, applies through a stimulation means in contact with the real body part tactile stimulation to a contacted location, and visually displays the movement of the virtual body part through the virtual reality according to the tracked motion and tactile information from the stimulation means to induce an ownership feeling that makes the user mistake the virtual body part for a real body part, and
wherein the program driven by the processor includes an instruction that induces the ownership feeling to the user, and then controls the real body part not to move, but displays an image in which the virtual body part performs a preset target movement in the virtual reality to the user to induce the motor imagery.

10. The guidance apparatus of claim 9, wherein the display means is configured as either a display device or a head mounted display (HMD) that is located to face a user's vision and is formed so that the real body part is not seen from the user's vision.

11. The guidance apparatus of claim 9, wherein the program driven by the processor includes an instruction that maps the real body part located so as not to be seen from a user's vision to the virtual body part corresponding to the real body part and generates an image by including the virtual body part in the virtual reality, and displays the generated image through a display means located to face the user's vision.

12. The guidance apparatus of claim 9, wherein the program driven by the processor generates a real-time image representing the movement of the virtual body part in the virtual reality according to the tracked motion, and provides real-time visual information to the user by displaying the generated real-time image through a display means and matches the real-time visual information and a real-time motor feeling in which the user moves the real body part together to transfer the ownership feeling to the virtual body part in the virtual reality.

13. The guidance apparatus of claim 12, wherein the program driven by the processor visually emphasizes and displays a region in which the movement is represented in the real body part according to the tracked motion in the same region in the virtual body part to generate the real-time image.

14. The guidance apparatus of claim 12, wherein the program driven by the processor simultaneously continues to provide the real-time visual information and the real-time motor feeling to the user over a preset reference time or reference intensity so that the user reaches a level of the ownership feeling to transfer the ownership feeling.

15. The guidance apparatus of claim 14, wherein the preset reference time or the reference intensity is set so that an electroencephalogram (EEG) signal measured from the user is equal to or greater than a threshold value.

16. The guidance apparatus of claim 9,
wherein the program driven by the processor includes an instruction that represents the movement of the virtual body part in the virtual reality according to the tracked motion, generates a real-time image visualizing and representing the tactile information on the virtual body part corresponding to the same time point and location at which the tactile stimulation is applied through the stimulation means, and provides real-time visual information to the user by displaying the generated real-time image through a display means and matches the real-time visual information and a real-time motor feeling in which the user moves the real body part, and the real-time tactile information recognized through the real body part together to transfer the ownership feeling to the virtual body part in the virtual reality.

17. The guidance apparatus of claim 16, wherein the simulation means is provided in plural and applies the stimulation to the real body part at different time points and locations, and the program driven by the processor represents the tactile information visualized in the contact region of the virtual body part in real time in response to the stimulation applied at different time points and locations through the plurality of stimulation means to induce the ownership feeling.

* * * * *